United States Patent [19]

Sukiennik et al.

[11] Patent Number: 4,908,026
[45] Date of Patent: Mar. 13, 1990

[54] FLOW DISTRIBUTION SYSTEM FOR ABSORBENT PADS

[75] Inventors: Corrine A. Sukiennik, Neenah, Wis.; Mollie M. Becker, Loreto B.C.S., Mexico

[73] Assignee: Kimberly-Clark Corporation, Neenah, Wis.

[21] Appl. No.: 945,934

[22] Filed: Dec. 22, 1986

[51] Int. Cl.$^4$ ............................................. A61F 13/16
[52] U.S. Cl. .................................................... 604/378
[58] Field of Search ................................. 604/378–385

[56] References Cited

U.S. PATENT DOCUMENTS

| | | | |
|---|---|---|---|
| 3,375,827 | 4/1968 | Bletzinger et al. | 128/290 |
| 3,491,759 | 1/1970 | Samuel | 128/290 |
| 3,518,726 | 7/1970 | Banks | 19/144.5 |
| 3,523,536 | 8/1970 | Ruffo | 128/287 |
| 3,528,421 | 9/1970 | Vaillancourt | 128/284 |
| 3,542,634 | 11/1970 | Such et al. | 161/88 |
| 3,593,717 | 7/1971 | Jones, Sr. | 128/290 |
| 3,693,622 | 9/1972 | Jones, Sr. | 128/290 |
| 3,736,931 | 6/1973 | Glassman | 128/290 |
| 3,749,627 | 7/1973 | Jones, Sr. | 156/268 |
| 3,759,262 | 9/1973 | Jones, Sr. | 128/290 |
| 3,805,790 | 4/1974 | Kaczmarzyk et al. | 128/290 |
| 3,888,248 | 6/1975 | Moore et al. | 128/290 |
| 3,949,127 | 4/1976 | Ostermeier et al. | 428/137 |
| 3,954,107 | 5/1976 | Chesky et al. | 128/290 |
| 3,967,623 | 7/1976 | Butterworth et al. | 128/287 |
| 4,079,739 | 3/1978 | Whitehead | 128/290 |
| 4,195,634 | 4/1980 | DiSalvo et al. | 128/290 |
| 4,321,924 | 3/1982 | Ahr | 128/287 |
| 4,323,069 | 4/1982 | Ahr et al. | 604/378 |
| 4,324,246 | 4/1982 | Mullane et al. | 604/370 |
| 4,333,462 | 6/1982 | Holtman et al. | 128/287 |
| 4,333,463 | 6/1982 | Holtman | 128/287 |
| 4,333,465 | 6/1982 | Wiegner | 128/290 |
| 4,341,207 | 7/1982 | Steer et al. | 128/155 |
| 4,341,217 | 7/1982 | Ferguson et al. | 128/290 |
| 4,392,861 | 7/1983 | Butterworth et al. | 604/366 |
| 4,397,644 | 8/1983 | Matthews et al. | 604/378 |
| 4,469,734 | 9/1984 | Minto et al. | 428/134 |
| 4,480,000 | 10/1984 | Watanabe et al. | 428/284 |
| 4,518,451 | 5/1985 | Luceri et al. | 156/202 |
| 4,531,945 | 7/1985 | Allison | 604/378 |
| 4,578,070 | 3/1986 | Holtman | 604/378 |
| 4,592,751 | 6/1986 | Gegelys | 604/378 |
| 4,596,567 | 6/1986 | Iskra | 604/368 |
| 4,608,292 | 8/1986 | Lassen | 428/131 |
| 4,623,340 | 11/1986 | Luceri | 604/378 |
| 4,704,112 | 11/1987 | Suzuki et al. | 604/379 |
| 4,755,413 | 7/1988 | Morris | 604/683 |

FOREIGN PATENT DOCUMENTS 0140560 5/1985 European Pat. Off. .
0165807 12/1985 European Pat. Off. .
2055586 3/1983 United Kingdom .
2124907 2/1984 United Kingdom .

*Primary Examiner*—Jerome L. Kruter
*Attorney, Agent, or Firm*—Paul Leipold; Thomas J. Connelly

[57] ABSTRACT

An absorbent article is disclosed having a liquid pervious liner, a liquid-impermeable backing member and an absorbent position therebetween. The liner contains a plurality of perforations extending completely therethrough which are arranged in a central area and spaced away from the longitudinal side edges of the article. The article also contains a flow zone control layer having a first surface in contact with the perforated central area of the liner and a second surface in contact with the absorbent. The flow zone control layer facilitates dispersion of body fluid along the length thereof before allowing a substantial amount of the fluid to pass into the absorbent. The preferred flow zone material is a meltblown polymer and the preferred perforated cover is spunbonded polypropylene.

22 Claims, 4 Drawing Sheets

FLOW DISTRIBUTION SYSTEM FOR ABSORBENT PADS

FIELD OF THE INVENTION

This invention relates to an absorbent article, particularly sanitary napkins used for absorption of human exudate. The adsorbent article contains a flow zone control layer which facilitates dispersion of body fluid along the length thereof before allowing a substantial amount of the fluid to pass into an absorbent.

BACKGROUND OF THE INVENTION

In the formation of absorbent articles for bodily excretions, one continuing problem is that the bodily excretions are usually directed at one portion of the absorbent pad, whereas the absorptive capacity is spread over a greater area. This may create an early failure problem if the exudate to be absorbed cannot be spread throughout the absorbent. If the fluid does not spread out through the absorbent, it may run off the edge of the saturated zone. Another disadvantage is that when the saturated absorbent in the primary flow area is compressed, for example when a person sits down, it may force the fluid out of the pad and cause rewetting. Such compression can also cause an overflow which can be uncomfortable to the wearer and which can result in stains to the undergarment.

Another problem to be overcome, in catamenial devices particularly, is that discharges can include fairly large pieces of tissue and blood clots that do not readily pass through a fine cover material. With sanitary napkins it would be desireable if the stained absorbent material did not exhibit the stains after absorption. It also would be desirable if feminine pads and other absorbent products could be visually examined to determine if they were almost saturated. Quite often with the absorption being into a target zone on the top of the pad and then spreading beneath the absorbent, it is not clear from top viewing when the pad is close to being saturated or when the target area is so close to being fully saturated that leakage may soon result.

In U.S. Pat. No. 4,423,101 issued to Willstead and French patent 1,477,127 issued to Cartiera Di Cairate, it is disclosed that the cover material may be perforated to aid in the passing of materials through the cover. In U.S. Pat. No. 4,480,000 issued to Watanabe et al. and U.S. No. 3,375,827 issued to Bletzinger et al., it has been proposed to interpose a layer between the permeable wrapper member and the main portion of the absorbent. Bletzinger et al. utilizes a compressed cellulosic material and indicates that the element spreads the exudate as it is absorbed.

There still remains a need for a pad that will provide even distribution of fluid within the pad, a cleaner surface to the pad, better concealment of fluid in the pad and less side leakage.

SUMMARY OF THE INVENTION

The general object of this invention is to provide a pad for absorbing human exudate that overcomes disadvantages of previous pads.

Another object of this invention is to provide a catamenial pad that provides better catamenial fluid distribution.

Still another object of this invention is to provide a feminine pad that has minimum side staining.

A further object of this invention is to provide a pad having a cleaner appearing surface after use.

Still further, an object of this invention is to provide uniform transfer of fluid into the absorbent of a pad for absorption of human exudate.

Other objects and advantages of the present invention will become more apparent to one skilled in the art upon reading the following description.

Briefly, this invention relates to a pad having a flow zone control layer adjacent the bodyside liner of the pad. The flow zone control layer is in contact with the absorbent on its lower side and with the inner surface of the bodyside liner on its upper surface to provide a fluid passage way from the surface to the absorbent. The flow zone control member would be located only in the middle portion of the pad. The bodyside liner is provided with perforation in the area of the flow zone control layer to aid in transfer of liquids to the flow zone control layer. The pad would also be provided with an impervious backing member on the side away from the body.

In a preferred embodiment, the flow zone control layer would be comprised of a meltblown polymer located in the central portion of the pad and not extending to any edge of the pad. The bodyside liner would be a spunbonded material having perforations of a hole size of between about 0.032 and about 0.081 inch with an open area in the perforated zone of about 22 to about 50 percent. The meltblown flow zone control layer further is preferably of a different color than the absorbent in order to provide indication when the pad needs changing.

DETAILED DESCRIPTION OF THE PREFERRED EMBODIMENTS

The pad of the invention provides improved fluid containment. The pad has less side staining and also less leakage at the front and back than previous pads. The pad provides improved removal of fluid from the permeable cover material residue on the cover material providing a drier and cleaner surface with less residue on the cover. The pad also provides an improved perception of comfort and cleanliness. The covered flow zone control layer further provides a perceived improvement in absorbency and gives the wearer the feeling that the absorbed material is held in the center of the pad.

The flow zone control layer also provides an indicator for when it is time to change the pad. This is when the fluid begins to extend beyond the flow zone control layer at the surface of the absorbent. The flow zone control layer further provides uniform transfer of fluid into the absorbent so as not to overload the center or target area during the early use of the pad.

Figure 1:
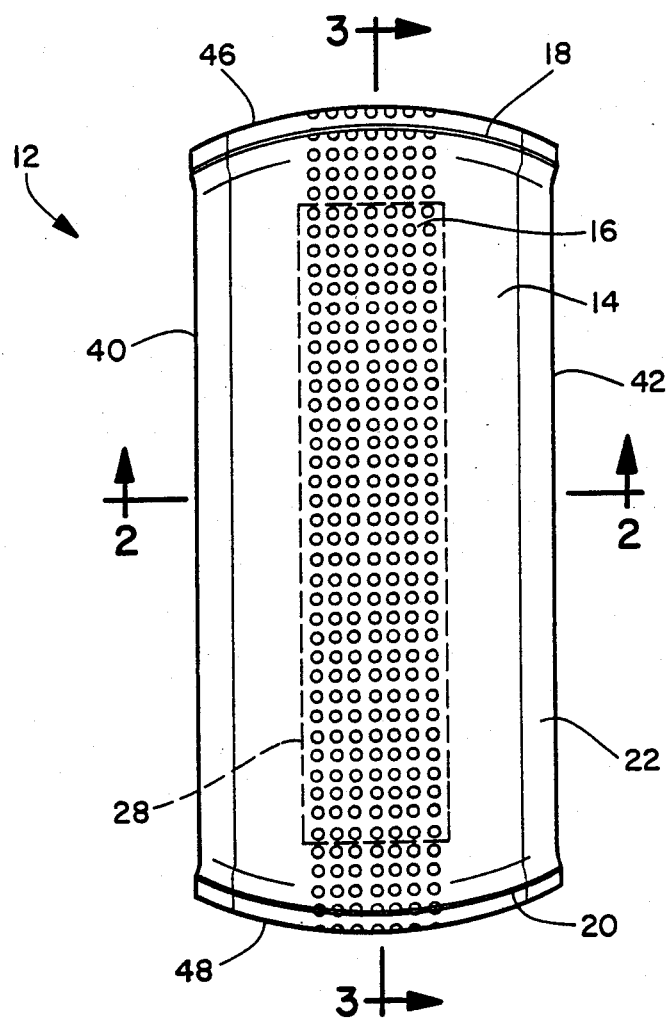
FIG. 1 is a top view of the pad of the invention.

Referring to FIG. 1, a pad 12 is provided with a fluid permeable liner 14 having a perforated longitudinal area 16. The pad 12 has end seals 18 and 20 which may be formed by adhesive or ultrasonic sealing. The linear 14 is wrapped under a fluid-impermeable backing member 22 and overlapped and sealed at 24. A flow zone control layer 28 is positioned below the perforated area 16.

Figure 2A:
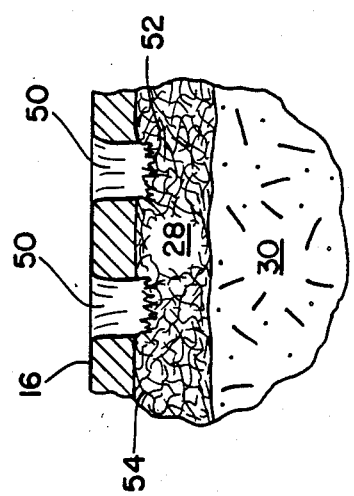
FIG. 2a is an enlarged view of a circled area shown in FIG. 2.
Figure 2:
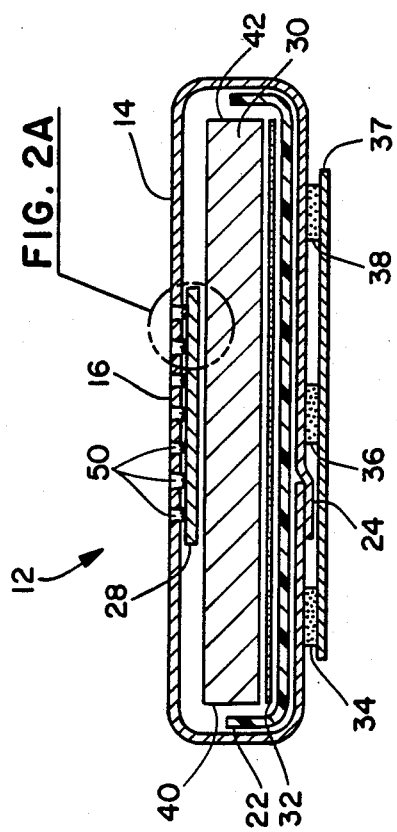
FIG. 2 is a sectional view, of the pad shown in FIG. 1 taken along cross-sectional line 2—2.
Figure 3:
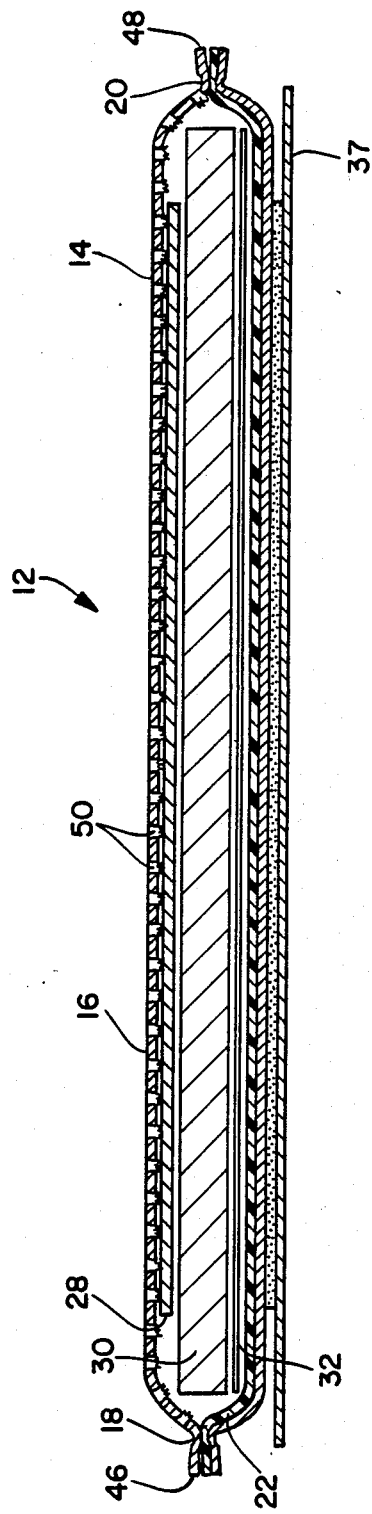
FIG. 3 is a cross-sectional view of the pad shown in FIG. 1 taken along line 3—3.

As illustrated in FIGS. 2 and 3, an absorbent 30 is adhesively connected to the backing member 22 by construction adhesive 32. The pad 12 is provided with one or more strips of a garment attachment adhesive 34, 36 and 38 that is provided by a peel strip 37 prior to use. The peel strip 37 is removed prior to attachment of the pad 12 to the wearer's garment (not shown) by the strips of garment adhesive 34, 36 and 38. The flow zone control layer 28, preferably formed of a meltblown material, does not extend to longitudinal side edges 40 and 42 of the pad 12 nor to ends 46 and 48 of the pad 12. Perforations 50 are formed in the liner 14 in an area generally corresponding to the flow zone control layer 28.

As best shown in FIG. 2a, the perforations 50, as a result of the perforating process, have loose elements 52 that act as sucker feet to become entangled with fuzzy, hairy meltblown fibers 54 of the flow zone control layer 28. The loose elements 52 are believed to aid in the transfer of liquid from the bodyside of the pad 12 to the flow zone control layer 28. Furthermore, the fibers 54 aids in the transfer of liquid through the flow zone control layer 28 into the absorbent 30. The flow zone control layer 28 is selected such that it will preferentially transfer fluid along its length prior to transferring the fluid to the absorbent 30. However, the hairy fibers 54 on its lower side aids in transfer of fluid to the absorbent 30. The meltblown fibers 54 allows better contact between the liner 14 and the absorbent 30. The meltblown fibers 54 frictionally by entanglement, adheres to the liner 14 and also the absorbent 30. Furthermore, the loose elements 52 aid in the transfer of fluid from the liner 14 to the flow zone control layer 28 and also to the absorbent 30 if fluid reaches the ends of the pad 12 where the loose elements 52 would contact the absorbent 30 rather than the flow zone control layer 28.

Figure 4A:
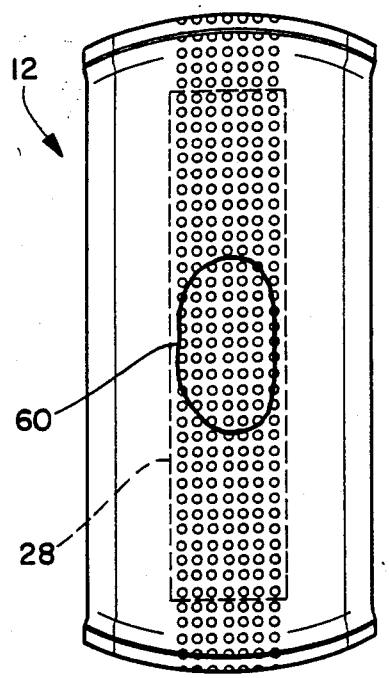
FIGS. 4a, 4b, 4c and 4d illustrate the pad of the invention as it is progressively wet by fluid.
Figure 4B:
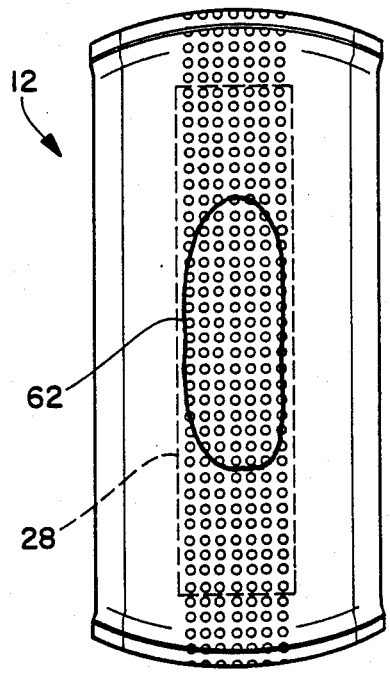
Figure 4C:
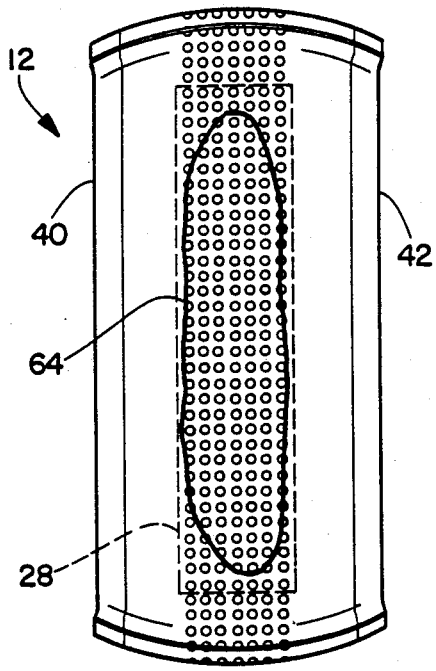
Figure 4D:
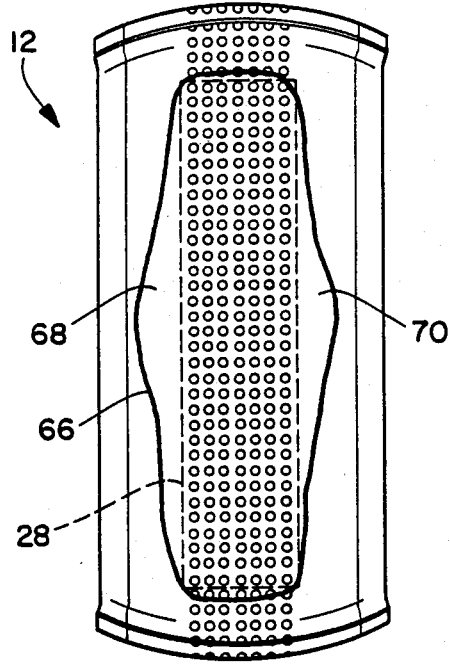

FIGS. 4a, 4b, 4c and 4d represent the views of the pad 12 as it is subjected to normal use. FIG. 4a illustrates the pad 12 as it is first contacted with bodily exudate such as catamenial fluid or menses. An initial stain or wet area 60 is located in the central portion of the pad 12 overlaying the flow zone control layer 28. FIG. 4b shows that as additional fluid reaches the pad 12, the stain or wet area extends along the direction of the flow zone control layer 28 and leaves a stained area 62. FIG. 4c illustrates the addition of still more fluid to the pad 12 that has continued to extend along the flow zone control layer 28 rather than to the longitudinal edges 40 and 42. A stained area 64 is now present which extends almost to the ends of the flow zone control layer 28. FIG. 4d illustrates the pad 12 when it is providing visual indication that it should be changed. A stained area 66 is present which has begun to extend outside the flow zone control layer 28 onto the absorbent 30. It should be noted that the fluid substantially fills the flow zone control layer 28 prior to being transferred into the absorbent 30 and staining areas 68 and 70. It should be noted that the fluid retained in the absorbent 30 will be in a greater area towards the bottom of the pad 12 than will show at the top. Therefore, the pad 12, depicted in FIG. 4d, is ready for changing but the fluid has not leaked to the longitudinal edges 40 and 42.

Figure 5:
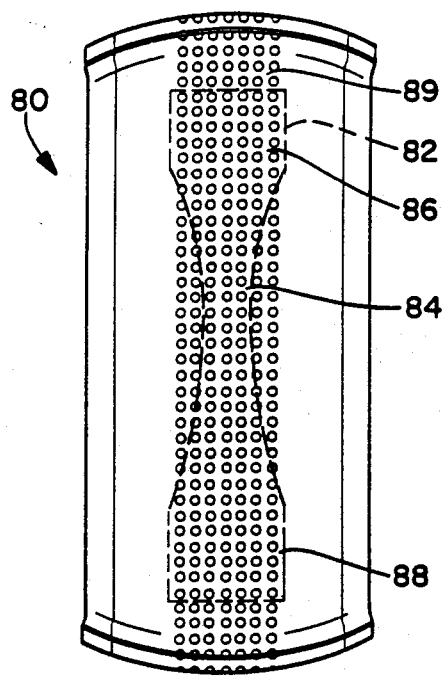
FIG. 5 illustrates a pad having an hourglass-shaped flow zone control layer.

FIG. 5 illustrates a pad 80 having a generally rectangular shape with a perforated area 89 extending along its longitudinal center line. The pad 80 is provided with a flow zone control layer 82 that is hourglass in shape, having a narrowed crotch portion 84 and ends 86 and 88. The crotch area is normally narrowed during use and this design may be desirable for transferring fluid to the ends 86 and 88.

Figure 6:
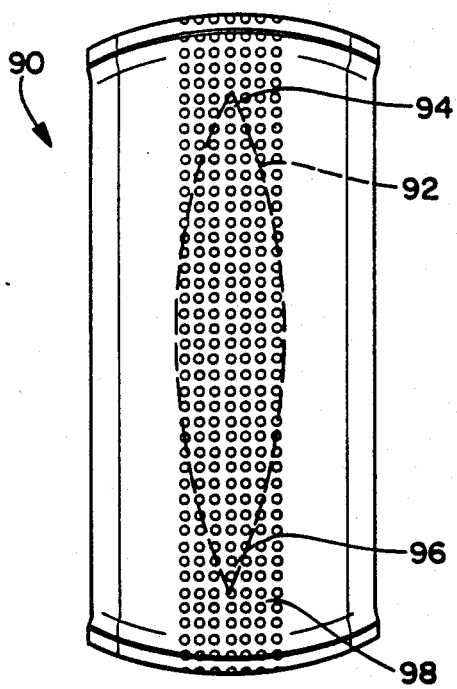
FIG. 6 illustrates a pad having an oval shaped flow zone control layer.

FIG. 6 illustrates a rectangular pad 90 having an oval shaped flow zone control layer 92 with ends 94 and 96. The pad 90 has a perforated area 98 extending along its longitudinal centerline. The oval shaped flow zone control layer 92 can provide a cleaner appearing pad in that when the flow zone control layer 92 becomes stained, it is less visible below portions of the liner, especially near the ends 94 and 96.

Figure 7:
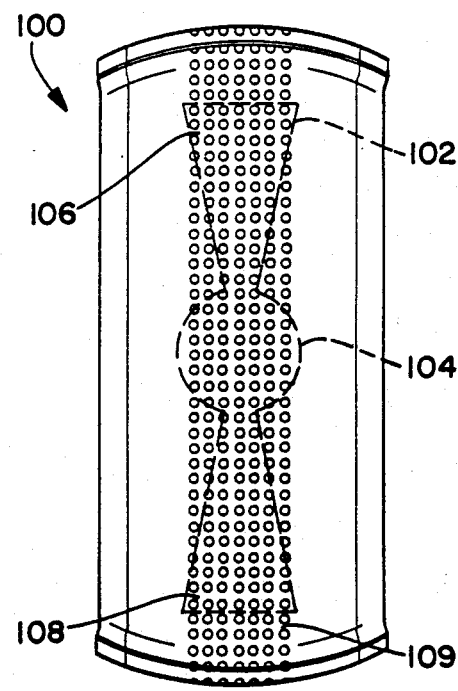
FIG. 7 illustrates a pad having a bow tie shaped flow zone control layer.

FIG. 7 illustrates a pad 100 with a flow zone control layer 102 having a generally bow tie shape. The flow zone control layer 102 has an enlarged center portion 104 in the crotch area of the pad 100 and end portions 106 and 108 that are narrower where they contact the center portion 104 and widen towards the ends. The pad 100 has a perforated area 109 extending along its longitudinal centerline. The pad 100 is visually pleasing and also indicates to the user a transfer of discharged material to the ends of the pad 100 from central target portion 104. It should be noted that in FIGS. 5, 6 and 7, the perforated areas 89, 98 and 109 respectively, are of uniform width and extend longitudinally between the ends of the respective pads. The perforated areas 89, 98 and 109 are easy to form as they may be formed continuously in line during production. However, it is possible that, with specialized perforating systems for cover perforating, the perforated area could be formed to correspond to the illustrated flow zone control layer if this is preferred.

Figure 8:
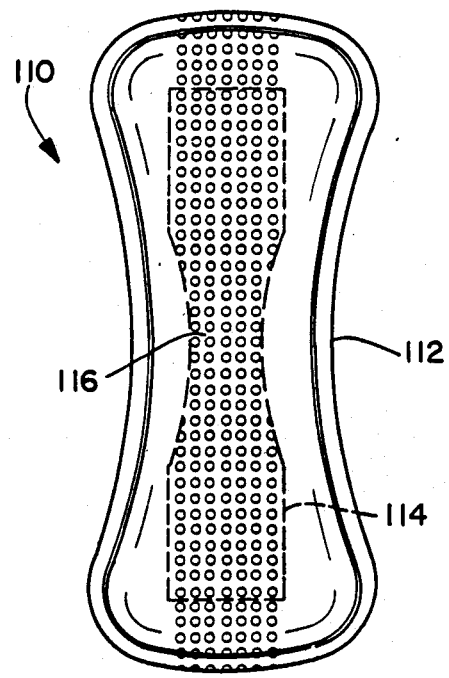
FIG. 8 illustrates an hourglass shaped pad having an hourglass shaped flow zone control layer.

Referring to FIG. 8, a pad 110 is shown having a generally hourglass shape with a narrow crotch portion 112. A flow zone control layer 114 is also hourglass in shape. The pad 110 further has a narrow perforated area 116 at the crotch portion 112. Hourglass shaped pads are known in the art, and the presents of the flow zone control layer 114 also could lead to improved performance.

The cover material forming the liquid pervious bodyside liner may be any suitable material that is pervious to liquids, nonirritating and which may be perforated. Typical of such materials are bonded carded webs of polyester, polypropylene, nylon or other heat-bondable fibers. Other materials that may be suitable are net materials or finely perforated film webs. A particularly preferred material is spunbonded polypropylene fabric. The most preferred spunbonded polypropylene webs have a weight of between about 18 and about 40 grams per square meter. An optimum weight is between about 30 and about 40 grams per square meter. A white uniform spunbonded material is desirable because the color exhibits good masking properties to hide liquid that has passed through it and the material has sufficient strength after being perforated in the longitudinal direction that the cover does not tear or fall apart in use. It is also possible that a composite bodyside liner material such as that disclosed in U.S. No. 4,397,644, issued to Matthews et al., could be utilized as the bodyside member and provided with perforations in the longitudinal center portion.

The flow zone control layer may be constructed of any material that will provide good fluid transfer from the bodyside liner to the flow zone control layer, along the flow zone control layer and to the lower bulk or mass absorbent of the pad. Typical of such materials are densified fluff, coform, carded webs and creped tissue. Rather than a hairy or fuzzy surface, it is believed that a mechanically roughened, high friction surface webs such as an embossed or creped body wadding or tissue would be suitable for this invention. A preferred material is meltblown polypropylene having a weight of between about 0.2 and about 2.0 ounces per square yard. This material has a frictional hairy, fibrous surface that will adhere to the bodyside liner and aid in fluid transfer from the bodyside liner to the flow zone control layer and also adhere to the absorbent and aid in fluid transfer from the flow zone control layer to the bulk absorbent. The preferred meltblown polypropylene is treated to be hydrophilic and will preferentially transfer to a bulk absorbent of devilicated cellulose fibers. The material may be a single sheet of about 1.0 to 2.0 ounces per square yard or folded to achieve that weight. The thickness is generally between about 1 and about 5 millimeters. The meltblown material may be perforated if desired. The meltblown material may also be colored a different color than the cover material and absorbent. A light blue, pink or peach color has been found to be desirable as these are pleasing feminine colors. The use of a different color than the absorbent also presents a target for the wearer and will indicate when the pad was not placed properly.

The meltblown material has a high surface fiber, fuzzy or hairy surface that, when placed in contact with the perforated cover sheet, has a high coefficient of friction. This high coefficient of friction is believed to aid in maintaining contact of the cover sheet and the flow zone control layer. The cover sheet, after being perforated, has descended fibers surrounding the raised perforation holes, above referred to as loose elements, that are believed to become entangled in the surface of the meltblown material. This provides good contact between the cover and the flow zone control layer during use and good fluid transfer from the cover to the fluid zone control layer. The loose elements in contact with the meltblown material creates a dry-adhesive condition adhering the contacted materials. The coefficient of friction has been found to be preferably greater than about 0.7. Generally, the coefficient of friction ranges between about 0.7 and about 1.2 when utilizing an apertured cover or spunbonded material and a meltblown flow zone control layer. Generally, the difference between the coefficient of friction of the apertured spunbond and the meltblown material, as compared with the unapertured spunbond and the same meltblown material, is between about 15 and about 45 percent lower for the unapertured material. Tests conducted on a group of three different unapertured spunbonded materials versus a meltblown material indicated ranges of coefficient of friction from 0.57 to 0.73. Coefficient of friction for apertured spunbonded material versus a meltblown material indicated ranges of coefficient of friction of between about 0.7 and about 1.1.

Table I sets forth coefficient of friction results comparing the frictional properties of a meltblown polymer in combination with perforated and unperforated spunbonded cover materials.

TABLE I

| Sample | COF* Forming Side of Meltblown | COF* Wire Side of Meltblown |
|---|---|---|
| A - unapertured | .72 | .67 |
| A - apertured | .90 | .82 |
| B - unapertured | .73 | .66 |
| B - apertured | 1.12 | .96 |
| C - unapertured | .65 | .57 |
| C - apertured | .87 | .76 |
| D - unapertured | .63 | .57 |
| D - apertured | .83 | .71 |

Meltblown about 2.65 oz./yard and about 1.2 mm thick
A = .8 oz./yd. - Kimberly-Clark's linear drawn Spunbonded Polypropylene
B = .7 oz./yd. - Lurgi Spunbonded Polypropylene
C = .8 oz./yd. - Kimberly-Clark's linear drawn fiber spunbond (modified cross section) (Lexington Mill)
D = .8 oz./yd. - Kimberly-Clark's linear drawn fiber spunbond (modified cross section) (Corinth Mill)
*Coefficient of Friction Average for four tests The coefficient of friction was determined by use of a Instron Tensile Tester. Utilizing this machine, the meltblown material was fastened to the platform of the tester. A sled of 200 grams had a strip of spunbonded cover material about 4.5 by 2.78 inches fastened to it. The sled was then pulled across the meltblown material. Tests were done of apertured and unapertured spunbond of the same structure. Testing was performed both on the meltblown wire side of the meltblown and the top or forming side of the meltblown. The coefficient of frictions are slightly higher on the forming side of the meltblown. A reading of the average force required to maintain the sled in motion over the apertured material is read as the force reading. This is divided by the weight of the sled to obtain a coefficient of friction which does not have units.

The absorbent forming the bulk absorbent of the pad may be any desired material. Typical of such materials are rayon, polyesters, coforms and combination of these absorbent fibers, and superabsorbents in combination with fibrous materials. A preferred material is devilicated wood fiber fluff as it is low in cost. The fluff may be wrapped in a tissue wrapping material as is standard in absorbent pad construction. The pad further may contain the cross-linked highly absorbent polymers ordinarily referred to as superabsorbents either as a separate layer or mixed with the fibers.

The baffle material may be any desirable liquid-impermeable member. It may be vapor-permeable if desired. Typical of such materials are polymer films such as polyethylene film. A preferred material is a polypropylene film as it is low cost and quiet.

The construction adhesives and garment attachment adhesives may be any of those typically utilized in formation of feminine pads, incontinence garments or diapers. Preferred garment attachment would be a single wide band adhesive pattern for maximum attachment strength.

The perforations in the cover are formed in the longitudinal center area generally corresponding with the flow zone control layer. The perforated area generally, for convenience of manufacture, will extend the entire longitudinal length of the pad. However, it would be satisfactory to have perforations only in the zone overlaying the flow zone control layer. Generally, the aperturing is such that it provides between about 20 and about 50 percent open area in the apertured area. A preferred amount of aperturing is between about 40 and about 45 percent open area to leave a large amount of remaining integrity in the spunbonded material that is apertured and still provide good transfer of menstrual fluids. The hole size of the perforation generally is between about 0.032 and about 0.091 inch. A preferred hole size is between about 0.06 and about 0.08 inch. The depth of aperture is preferred to be greater than the thickness of the cover liner to create the loose element effect as discussed above. A variety of regular or irregular aperturing patterns may be utilized.

The width of the central area of longitudinal aperturing may be between about ¾ and about 2 inches wide, with the wider range being utilized in wider pads and the narrower range being utilized in narrow pads. Generally, feminine pads may extend in a width between about 1½ and about 3½ inches. The meltblown flow zone control layer generally has a width corresponding to that of the apertured area. In a typical feminine pad, the meltblown flow zone control layer would have a length of between about 4.5 and about 6.5 inches. This length is enough to insure exposure of the flow zone control layer to the target zone without getting the flow zone control layer too close to the edges of the pad.

The cover material for the bodyside liner may be treated with a surfactant if desired to aid in absorption of liquid. However, if the properties of the bodyside liner allow its use without treatment with a surfactant, a drier feeling cover will result.

While the invention has been discussed with prime consideration given to catamenial devices, the invention can also find use in other garments and devices for absorption of human exudate. Such other uses include small incontinence pads of the shield variety whose size is only somewhat larger than a typical feminine pad, larger incontinent garments such as the loincloth-like undergarments and the largest diaper-like adult incontinence garments. The invention is also suitable for use in diapers for infant care.

While flat rectangular pads have been described, the invention is also suitable for use with shaped pads. Such pads include those shaped with an outer-impermeable baffle of a molded foam, those shaped by elasticized edges and those shaped by having a preformed contoured absorbent structure. The preferred meltblown insert is easily shaped to any desired shape or dimension.

The described invention has advantages in the ease of formation. The utilization of a generally rectangular member that is merely laid onto an absorbent prior to being covered with a bodyside permeable liner is easy to form. Furthermore, in-line perforation of a longitudinal portion of the cover is easy to carry out as a line process. In addition, there is no need for adhesives or complicated expensive layered cover structures. The invention produces a very effective low-cost pad.

While the invention has been illustrated with specific examples and materials, there are other variations in materials and form that will be apparent to one of ordinary skill in the art. The scope of the invention is only intended to be limited by the scope of the claims attached hereto.

We claim:
1. An absorbent article comprising:
 (a) a liquid pervious liner designed to be positioned adjacent to the body of a wearer, said liner having a plurality of perforations extending completely therethrough which are arranged in a central area and spaced away from the longitudinal side edges thereof;
 (b) a liquid-impermeable backing member;
 (c) absorbent means for absorbing body fluids positioned between said liner and said backing member; and
 (d) flow zone control means for facilitating dispersion of body fluid along the length thereof before allowing said fluid to pass into said absorbent, said flow zone control means being positioned between said central area of said liner and said absorbent means, and said flow zone control means has a coefficient of friction with said liner of between about 0.7 and 1.1.

2. The absorbent article of claim 1 wherein said flow zone control means is a fibrous layer having a first surface in contact with said liner and a second surface in contact with said absorbent.

3. The absorbent article of claim 2 wherein said fibrous layer is formed of meltblown polymer fibers.

4. The absorbent article of claim 3 wherein said fibrous layer is a different color than said absorbent.

5. The absorbent article of claim 4 wherein said fibrous layer is a darker color than said absorbent.

6. The absorbent article of claim 1 wherein said flow zone control means is a layer of fibrous material which is located below said perforated central area of said liner and is spaced away from said longitudinal side edges of said liner.

7. The absorbent article of claim 1 wherein said flow zone control means is in direct contact with said absorbent and is spaced away from the longitudinal side edges of said absorbent.

8. An absorbent article comprising:
 (a) a liquid pervious liner designed to be positioned adjacent to the body of a wearer, said liner having a plurality of perforations extending completely therethrough which are formed in a central area and spaced away from the longitudinal side edges thereof;
 (b) a liquid-impermeable backing member;
 (c) absorbent means for absorbing body fluids, said absorbent means being positioned between said liner and said backing member; and
 (d) a flow zone control layer having a first surface in contact with said perforated central area of said liner and a second surface in contact with said absorbent, said flow zone control layer facilitating dispersion of body fluid along the length thereof before allowing a substantial amount of said fluid to pass into said absorbent means, and wherein said first surface has a coefficient of friction with said liner of between about 0.7 and 1.1.

9. The absorbent article of claim 8 wherein said flow zone control layer is distally spaced from the periphery of said liner.

10. The absorbent article of claim 8 wherein said flow zone control layer is distally spaced from the periphery of said absorbent means.

11. The absorbent article of claim 10 wherein said flow zone control layer is formed of meltblown polymer fibers and is hydrophilic.

12. The absorbent article of claim 8 wherein said liner contains a plurality of perforations arranged in a narrow strip approximate the longitudinal central axis of said article, said plurality of perforations extending to opposite ends of said article.

13. The absorbent article of claim 12 wherein said plurality of perforations cause a portion of said liner material to be displaced downward and extend into said flow zone control layer thereby facilitating passage of body fluid into said layer.

14. The absorbent article of claim 8 wherein said plurality of perforations create an open area of about 20 to 50% of the total surface area of said liner.

15. An absorbent pad comprising:
(a) a liquid pervious liner designed to be positioned adjacent to the body of a wearer, said liner having a plurality of perforations extending completely therethrough which are formed in a central area and spaced away from the longitudinal side edges thereof;
(b) a liquid-impermeable backing member;
(c) absorbent means for absorbing body fluids, said absorbent means being positioned between said liner and said backing member; and
(d) a flow zone control layer lying beneath said perforated central area of said liner and positioned in direct contract with both said liner and said absorbent, said flow zone control layer having a distinctive shape and a surface area smaller than the total surface area of said perforated portion of said liner, said flow zone control layer facilitating dispersion of body fluid along the length thereof before allowing a substantial amount of said fluid to pass into said absorbent means, and said flow zone control layer having a coefficient of friction with said liner of between about 0.7 and 1.1.

16. The absorbent pad of claim 15 wherein said flow zone control layer has an oval shape.

17. The absorbent pad of claim 15 wherein said flow zone control layer has an hourglass shape.

18. The absorbent pad of claim 16 wherein said flow zone control layer has an enlarged portion located at the longitudinal center of said pad and a pair of appropriately aligned triangular members extending outward from said enlarged portion, said members have a greater width at their distal ends.

19. The absorbent pad of claim 15 wherein said flow zone control layer is a different color than said liner.

20. An absorbent pad comprising:
(a) a liquid pervious liner constructed of a spunbonded material and designed to be positioned adjacent to the body of a wearer, said liner having a plurality of perforations extending completely therethrough which are formed in a central area and spaced away from the longitudinal side edges thereof;
(b) a liquid-impermeable backing member;
(c) absorbent means for absorbing body fluid, said absorbent means being positioned between said liner and said backing member; and
(d) a flow zone control layer constructed of a meltblown material having a first surface in contact with said perforated central area of said liner and a second surface in contact with said absorbent, said flow zone control layer facilitating dispersion of body fluid along the length thereof before allowing a substantial amount of said fluid to pass into said absorbent means, and said flow zone control layer having a coefficient of friction with said liner of between about 0.7 and 1.1.

21. An absorbent article comprising:
(a) a liquid pervious liner designed to be positioned adjacent to the body of a wearer, said liner having a plurality of perforations extending completely therethrough which are arranged in a central area and spaced away from the longitudinal side edges thereof;
(b) a liquid-impermeable backing member;
(c) absorbent means for absorbing body fluids positioned between said liner and said backing member; and
(d) flow zone control means for facilitating dispersion of body fluid along the length thereof before allowing said fluid to pass into said absorbent, said flow zone control means being positioned between said central area of said liner and said absorbent means, and the coefficient of friction between said perforated liner and said flow zone control means is about 15 to 45% higher than the coefficient of friction between a non-perforated liner and said flow zone control means.

22. An absorbent article comprising:
(a) a liquid pervious liner designed to be positioned adjacent to the body of a wearer, said liner having a plurality of perforations extending completely therethrough which are formed in a central area and spaced away from the longitudinal side edges thereof;
(b) a liquid-impermeable backing member;
(c) absorbent means for absorbing body fluids, said absorbent means being positioned between said liner and said backing member; and
(d) a flow zone control layer having a first surface in contact with said perforated central area of said liner and a second surface in contact with said absorbent, said flow zone control layer facilitating dispersion of body fluid along the length thereof before allowing a substantial amount of said fluid to pass into said absorbent means, and the coefficient of friction between said perforated portion of said liner and said flow zone control layer is about 15 to 45% higher than the coefficient of friction between a non-perforated liner and said flow zone control layer.

* * * * *